(12) United States Patent
Zamborini et al.

(10) Patent No.: US 8,383,412 B2
(45) Date of Patent: Feb. 26, 2013

(54) SENSORS AND SWITCHES FOR DETECTING HYDROGEN

(75) Inventors: Francis P. Zamborini, Louisville, KY (US); Radhika Dasari, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 387 days.

(21) Appl. No.: 12/609,669

(22) Filed: Oct. 30, 2009

(65) Prior Publication Data

US 2010/0108529 A1 May 6, 2010

Related U.S. Application Data

(60) Provisional application No. 61/109,812, filed on Oct. 30, 2008.

(51) Int. Cl.
*G01N 15/06* (2006.01)
*G01N 33/00* (2006.01)
*G01N 33/48* (2006.01)

(52) U.S. Cl. .............. 436/144; 422/83; 422/98; 29/592; 29/592.1; 436/43; 436/149

(58) Field of Classification Search .................. 422/83, 422/98; 29/592, 592.1; 436/43, 144, 149
See application file for complete search history.

(56) References Cited

U.S. PATENT DOCUMENTS

| | | |
|---|---|---|
| 6,814,845 B2 | 11/2004 | Wilson et al. |
| 7,171,841 B2 | 2/2007 | Xu et al. |
| 7,367,215 B2 | 5/2008 | Monty et al. |
| 7,416,702 B2 | 8/2008 | Yamaguchi et al. |
| 2006/0021881 A1 | 2/2006 | Soundarrajan et al. |
| 2007/0140908 A1 | 6/2007 | Mizguchi et al. |
| 2007/0240491 A1 | 10/2007 | Pavlovsky et al. |
| 2008/0106276 A1 | 5/2008 | Penner et al. |
| 2008/0221806 A1 | 9/2008 | Bryant et al. |

OTHER PUBLICATIONS

Cheng et al., "Self-assembly of Metallic Nanowires From Aqueous Solution," Nano lett, vol. 5, 2005, pp. 175-178.
Christofides, Mandelis A., "Solid State Sensors for Trace Hydrogen Gas Detection," J. Appl. Phys., 68, 1990, pp. 1-30.
Favier et al., "Hydrogen Sensors and Switches from Electrodeposited Palladium Mesowire Arrays," Science, 293, 2001, pp. 2227-2231.
Haynes et al., "Electrospun Conducting Polymer-Based Sensors for Advanced Pathogen Detection," IEEE Sensors Journal, 8(6), 2008, pp. 701-705.
Ibanez et al., "Ozone-and thermally activated films of palladium monolayer-protected clusters for chemiresistive hydrogen sensing," Langmuir, 22, 2006, pp. 9789-9796.
Ibanez et al., "Reactivity of hydrogen with solid-state films of alkylamine-and tetraoctylammonium bromide-stabilized Pd, PdAg, and PdAu nanoparticles for sensing and catalysis applications," J. Am. Chem. Soc., 130, 2008, pp. 622-633.

(Continued)

*Primary Examiner* — Brian J Sines
(74) *Attorney, Agent, or Firm* — Stites & Harbison PLLC; Terry L. Wright

(57) ABSTRACT

Sensors and switches for detecting hydrogen include an electrically-insulating support; a first and second electrode; and a palladium structure alone or in combination with an organic insulating film. The palladium structures of the sensors are deposited on and contact a first electrode and a portion of the palladium structure extends to and contacts the second electrode to create a conductive path. The palladium structures of the switches are deposited on and contact a first electrode and a portion of the palladium structures extend to and contact an organic insulating film deposited on the second electrode. Upon exposure of the switch to hydrogen, portions of the palladium structure extend through the film and contact the second electrode to create a conductive path. Methods of detecting hydrogen and methods of fabricating a sensor for detecting an analyte of interest are also provided.

10 Claims, 6 Drawing Sheets

OTHER PUBLICATIONS

Kim et al., "Temperature-dependent molecular conduction measured by the electrochemical deposition of a platinum electrode in a lateral configuration," Applied Physics Letters, 85(20), 2004, pp. 4756-4758.

Kim et al., "Electrical transport measurement of molecular device fabricated by electrochemical deposition of platinum electrode," Thin Solid Films, 499, 2006, pp. 196-200.

Kong et al., "Functionalized Carbon Nanotubes for Molecular Hydrogen Sensors," Adv. Mater., 13(18), 2001, pp. 1384-1386.

Peschka W., "Hydrogen: The future cryofuel in internal combustion engines," Int. J. Hydrogen energy, 23(1), 1998, pp. 27-43.

Sakamoto et al., "Electrical resistance measurements as a function of composition of palladium—hydrogen (deuterium) systems by a gas phase method," J. Phys.: Condens. Matter., 8(19), 1996, pp. 3399-3411.

Shirsat et al., "Polyaniline nanowires-gold nanoparticles hybrid network based chemiresistive hydrogen sulfide sensor," Applied Physics Letters, 94 (083502), 2009, pp. 1-3.

Van Blarigan et al, "A Hydrogen Fuelled Internal Combustion Engine Designed for Single Speed/Power Operation," Int. J. Hydrogen Energy, vol. 23, No. 7, 1998, pp. 603-609.

Walter et al., "Palladium mesowire arrays for fast hydrogen sensors and hydrogen-actuated switches," Anal. Chem., 74, 2002, pp. 1546-1553.

Yu et al., "Fabrication of Palladium Nanotubes and Their Application in Hydrogen Sensing," Chem Mater, vol. 17, 2005, pp. 3445-3450.

Yun et al., "Electrochemically Grown Wires for Individually Addressable Sensor Arrays," Nano Letters, 4(3), 2004, pp. 419-422.

Ibanez et al., "Reactivity of Hydrogen with Solid-State Films of Alkylamine-and Tetraoctylammonium Bromide-Stabilized Pd, PdAg, and PdAu Nanoparticles for Sensing and Catalysis Applications," J. Am. Chem. Soc., 130(2), 2008, 622-633/.

ISA/US, International Search Report and Written Opinion for International Application No. PCT/US09/62787, mailed Jan. 12, 2010.

US 8,383,412 B2

SENSORS AND SWITCHES FOR DETECTING HYDROGEN

RELATED APPLICATIONS

This application claims priority to U.S. Provisional Application Ser. No. 61/109,812, filed Oct. 30, 2008, the entire disclosure of which is incorporated herein by this reference.

GOVERNMENT INTEREST

Subject matter described herein was made with U.S. Government support under Grant Number CHE-0518561 awarded by the National Science Foundation. The government has certain rights in the described subject matter.

TECHNICAL FIELD

The presently-disclosed subject matter relates to sensors and switches for detecting hydrogen, as well as methods of making and using the same. In particular, the presently-disclosed subject matter relates to sensors and switches for detecting hydrogen that make use of palladium structures alone or in combination with an organic insulating film. The presently-disclosed subject matter further describes methods of fabricating a sensor for detecting an analyte of interest whereby metal/organic/metal junctions are produced.

BACKGROUND AND GENERAL CONSIDERATIONS

Hydrogen ($H_2$) is a useful energy source that has the potential to reduce the need for fossil fuels in the future, and may someday replace or serve as an important alternative to the current fossil-based transportation fuels [9-11]. Indeed, a great deal of effort has been put forth to develop $H_2$-fueled motor vehicles in order to fulfill increasing energy demands for transportation. Also, $H_2$ is present as a common reagent in industry and is used as an $O_2$ scavenger in metallurgy, in hydrocracking for refined fuels, and in degradation of synthetic materials. However, utilizing $H_2$ can be dangerous, as $H_2$ has one of the lowest flash points ($-253°$ C.) of any energy source, making it highly explosive in air above 4% $H_2$ by volume [12]. Accordingly, one of the aims in fuel cell research is to safely store and release $H_2$ in a controlled manner. For these reasons, it is important to develop simple, reliable, low-cost sensors for the detection of $H_2$ over a range of concentrations.

Previously, arrays of palladium (Pd) mesowires have been synthesized by electrochemical deposition of Pd on the step-edges of highly-oriented pyrolytic graphite (HOPG), and the resistance change of these arrays in the presence of $H_2$ has been examined after the arrays were transferred to a glass substrate and electrical contacts to the arrays were made [1,2]. In contrast to most Pd-based $H_2$ sensing devices, which exhibit an increase in resistance in the presence of $H_2$ due to the formation of the more resistive $PdH_x$ [3,4], the Pd mesowire arrays exhibited a significant decrease in resistance due to the formation of break junctions within the mesowires upon volume expansion of the $PdH_x$ [1,2]. These devices quantitatively detected $H_2$ from 2 to 10% reversibly with 75 ms response times.

$H_2$ sensing has also been performed with films of Pd nanoparticles prepared by physical deposition or chemical methods [5,6]. However, these Pd nanoparticle-based sensors also contain nanoscale gaps and operate on similar principles as the mesowire array[1,2]. Other nanoscale materials used for $H_2$ sensing include carbon [7] and Pd nanotubes [8], which operate on different principles, but display low detection limits.

In any event, known methods and devices for detecting $H_2$ are only capable of detecting $H_2$ after assembling various sensors in a complicated multi-step process involving synthesis, assembly, and contact formation, or are only capable of assembling sensors that are unable to be constructed in a highly parallel fashion or with a near 100% success rate. Furthermore, none of the known methods and devices for detecting $H_2$ have sufficiently provided a sensor whereby metal electrodeposition is used to make direct contract between a deposited metal and one or more electrodes, which is of great importance in eliminating the need for multi-step processes involving synthesis, assembly, and contact formation.

SUMMARY

This summary describes several embodiments of the presently-disclosed subject matter, and, in many cases, lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this summary or not. To avoid excessive repetition, this summary does not list or suggest all possible combinations of such features.

The presently-disclosed subject matter includes sensors and switches for detecting hydrogen ($H_2$), as well as methods of making and using the same, that make use of palladium (Pd) structures alone or in combination with an organic insulating film.

In some embodiments, a sensor for detecting $H_2$ is provided that includes an electrically-insulating support; a first electrode and a second electrode that are positioned at a distance from one another and affixed to the support; and a Pd structure that is deposited on and contacts the first electrode such that at least a portion of the Pd structure extends to and contacts the second electrode, thus creating a conductive path between the first electrode and the second electrode. In some embodiments, the Pd structure that is deposited on the first electrode is electrochemically deposited on the first electrode.

In some embodiments, the sensors for detecting $H_2$ disclosed herein are used in a method of detecting $H_2$ in a gas sample by: providing a sensor in accordance with the presently-disclosed subject matter; applying a voltage potential along the conductive path between the first electrode and the second electrode of the sensor; exposing the sensor to the gas sample; and then detecting any decreases in conductivity along the conductive path between the first electrode and the second electrode to thereby detect $H_2$ in the gas sample. In some embodiments of the methods for detecting $H_2$ disclosed herein, an exemplary sensor for detecting $H_2$ is used to detect a concentration of $H_2$ in a gas sample of as low as 0.11%.

Further provided, in some embodiments of the presently-disclosed subject matter, are switches for detecting $H_2$. In some embodiments, a switch for detecting $H_2$ is provided that includes an electrically-insulating support; a first electrode and a second electrode that are positioned at a distance from one another and affixed to the support; an organic insulating film that is deposited on the second electrode; and a Pd structure that is deposited on and contacts the first electrode such that at least a portion of the Pd structure extends to and contacts the organic insulating film. In some embodiments, upon exposure of an exemplary switch to $H_2$, the portion of the Pd structure, which is in contact with the organic insulating film, extends through the organic insulating film and contacts the second electrode to create a conductive path between the first electrode and the second electrode.

In some embodiments, the Pd structure that is deposited on the first electrode of an exemplary switch is electrochemically deposited on the first electrode. Further, in some embodiments, the organic insulating film that is deposited on the second electrode is deposited on the second electrode by electropolymerization. In some embodiments, the organic insulating film of an exemplary switch is comprised of phenol, aniline, pyrole, or combinations thereof. For example, in some embodiments, electropolymerizing phenol on the second electrode of an exemplary switch creates an organic insulating film on the second electrode that is a polyphenol film.

Similar to the sensors for detecting $H_2$ discussed above, in some embodiments, the switches for detecting $H_2$ disclosed herein can be used in a method of detecting $H_2$ in a gas sample. In some embodiments, a method of detecting $H_2$ in a sample includes providing a switch for detecting $H_2$ in accordance with the presently-disclosed subject matter; applying a voltage potential between the first electrode and the second electrode; exposing the switch to a gas sample; and then detecting a current between the first electrode and the second electrode to thereby detect $H_2$ in the gas sample. In some embodiments of the methods for detecting $H_2$ disclosed herein, an exemplary switch for detecting hydrogen can be used to detect a concentration of $H_2$ in a gas sample of as low as 1.0%.

With regard to the electrodes of the exemplary sensors and switches for detecting $H_2$ disclosed herein, in some embodiments, the electrodes can include multiple fingers that can be aligned parallel with one another such that the first and second electrode are in an interdigitated configuration. In some embodiments of the presently-disclosed sensors and switches for detecting $H_2$, the distance between the first electrode and the second electrode is about 5 micrometers.

Still further provided, in some embodiments of the presently-disclosed subject matter, are methods for fabricating a sensor that is capable of detecting an analyte of interest. In some embodiments, a method of fabricating a sensor for detecting an analyte of interest is provided that comprises positioning a first electrode and a second electrode at a distance from one another on an electrically-insulating support; electropolymerizing a compound capable of producing an organic insulating film on the second electrode attached to the support; and electrodepositing a metal on the first electrode attached to the support such that at least a portion of the metal extends to and contacts the organic insulating film.

In some embodiments of the methods for fabricating a sensor disclosed herein, the metal electrodeposited on the first electrode is selected from silver (Ag), Pd, or combinations thereof. Further, in some embodiments, the compound capable of producing the organic insulating film is selected from phenol, aniline, pyrole, or combinations thereof. In some embodiments, the compound is phenol, such that the organic insulating film that is deposited on the second electrode is a polyphenol film.

In some embodiments of the presently-disclosed methods for fabricating a sensor, a method for fabricating a sensor for detecting an analyte of interest is provided that further comprises the step of varying a thickness of the organic insulating film to change a response and a recovery time of the sensor. In some embodiments, varying the thickness of the organic insulating film is accomplished by varying a number of electropolymerization cycles.

Advantages of the presently-disclosed subject matter will become evident to those of ordinary skill in the art after a study of the description, Figures, and non-limiting Examples in this document.

DESCRIPTION OF THE DRAWINGS

FIG. 1A) and switches for detecting hydrogen ("$H_2$ switches"; FIG. 1B) in accordance with the presently-disclosed subject matter.

DESCRIPTION OF EXEMPLARY EMBODIMENTS

Figure 1:
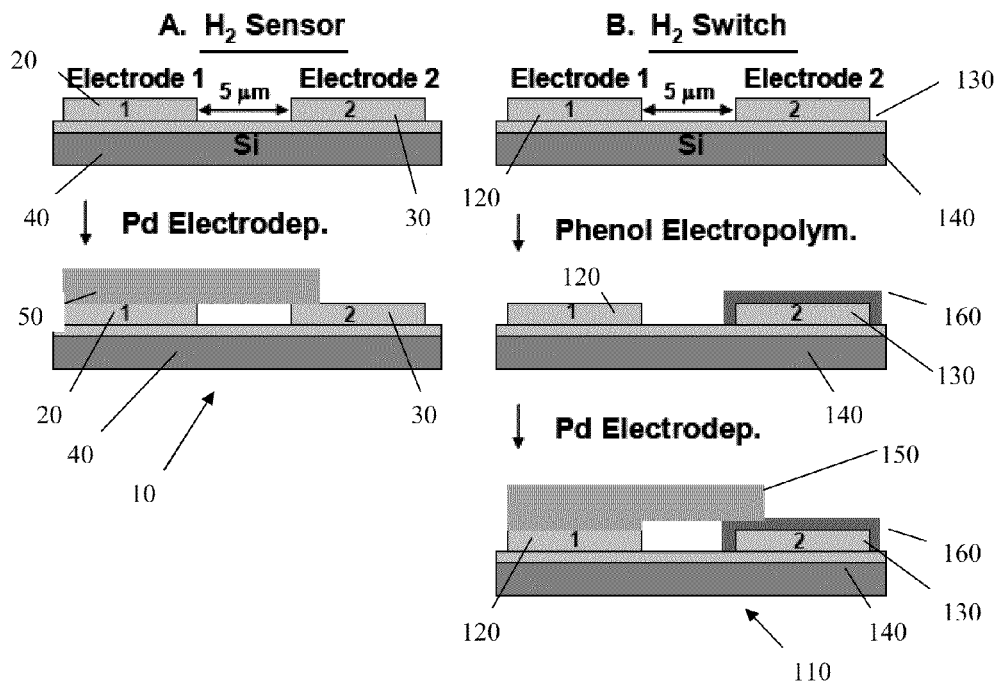
FIGS. 1A and 1B are schematic diagrams showing an exemplary method for fabricating sensors for detecting hydrogen ("$H_2$ sensors"

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom.

While the following terms are believed to be well understood by one of ordinary skill in the art, definitions are set forth to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a," "an," and "the" refer to "one or more" when used in this application, including the claims. Thus, for example, reference to "a sensor" includes a plurality of such sensors, and so forth.

Unless otherwise indicated, all numbers expressing quantities of ingredients, properties such as reaction conditions, and so forth used in the specification and claims are to be understood as being modified in all instances by the term "about." Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods.

The presently-disclosed subject matter provides sensors and switches for detecting hydrogen ($H_2$), as well as methods of making and using the same, whereby palladium (Pd) structures are utilized either alone or in combination with an organic insulating film.

It has been observed that by electrodepositing a metal (e.g., Pd) or by combining electrodeposition of a metal and electropolymerization of an organic compound capable of producing an organic insulating film (e.g., phenol) at micro-gap electrodes, metal-electrode or metal-organic-electrode junctions can be created that advantageously can be used to provide controlled responses to $H_2$, such that sensors and switches for detecting $H_2$ can effectively be created that avoid the problems present in prior sensors and switches for detecting $H_2$. In particular, the sensors and switches for detecting $H_2$ described herein include the benefits of: 1) forming a direct contact between metal structures and electrodes during synthesis, which eliminates the need for multi-step processes involving transfer, assembly, and contact formation that is common in electronic-based micro-/nano-sensing devices, and which lead to long fabrication times and device failures; 2) providing a simple, fast, highly parallel process with a near 100% success rate; and, 3) providing an approach for fabricating sensors and switches that may be used in fabricating a wide range of metal/organic/metal junctions. As such, the presently-disclosed subject matter also provides a method for fabricating a sensor, which may be used to fabricate a variety sensing devices for various applications.

FIG. 1A is a schematic diagram showing an exemplary method of making a sensor for detecting $H_2$ in accordance with the presently-disclosed subject matter. In this exemplary implementation, an exemplary sensor 10 for detecting $H_2$ is fabricated by initially positioning a first electrode 20 and a second electrode 30 at a distance from one another and affixing the electrodes 20, 30 to an electrically-insulating support 40. Various materials that resist the flow of electrical current can be used to provide an electrically-insulating support in accordance with the presently-disclosed subject matter, and thus can be used to support or separate electrical conductors (e.g., electrodes) while still providing low background conductivity or without allowing current to travel via the support itself. For example, in some embodiments, the exemplary electrically-insulating support 40 can be comprised of materials such as silicon/silicon oxide, other silicate materials such as micas and silicon nitrides, glass, porcelain, composite materials, polymers such as plastics, and ceramics. As will be recognized by those of ordinary skill in the art, each of the foregoing materials can be used to provide an electrically-insulating support onto which a first electrode and a second electrode can be affixed.

The first electrode 20 and the second electrode 30 of an exemplary sensor 10 for detecting $H_2$ can be comprised of any electrically-conductive material through which an electric current may enter and leave. Such electrodes are known to those of ordinary skill in the art and include, but are not limited to, silver, gold, platinum, chromium, titanium, palladium, copper, indium-tin-oxide, or conductive carbon electrodes. Further, as will also be recognized by those of ordinary skill in the art, various methods can be used to affix electrodes to a support such as evaporating, sputtering, or electrochemically depositing electrodes on an electrically-insulating support, as well as the utilization of conductive paints or photolithography procedures. For example, in some embodiments of the presently-disclosed subject matter, gold electrodes can be fabricated by photolithography and affixed to a silicon support by sputtering and depositing gold over a suitable adhesion layer such as a titanium adhesion layer.

As noted, an exemplary sensor 10 for detecting $H_2$ of the presently-disclosed subject matter is comprised of at least a first electrode 20 and a second electrode 30 that are positioned at a distance from one another. Typically, and as discussed further below with respect to the Pd structures 50 utilized in conjunction with the presently-disclosed subject matter, a criterion regarding the distance between the two electrodes 20, 30 is that the Pd structures 50 deposited on the first electrode 20 are able to extend across the gap between the electrodes 20, 30 and thus contact the second electrode 30 to create a conductive path between the first electrode 20 and the second electrode 30. The ability of a Pd structure to form a connection between two electrodes can occur at distances as long as tens to hundreds of micrometers depending on the length and amount of Pd materials used to make the connection. In some embodiments, however, to allow the Pd structures 50 to make a connection in a reasonable amount of time (e.g., a few minutes) and provide sufficient conductive path between the two electrodes 20, 30, a distance of less than 10 micrometers between the two electrodes 20, 30 is used. In the schematic diagram shown in FIG. 1A, the distance between the electrodes 20, 30 is about 5 micrometers.

In some embodiments of the presently-disclosed sensors for detecting $H_2$, the electrodes 20, 30 can include one or more fingers such that the first electrode 20 and the second electrode 30 can be arranged in an interdigitated configuration. For example, as shown in FIGS. 2A and 2B, in some embodiments, the first electrode 20 and the second electrode 30 are each comprised of about 5 to about 7 fingers that are aligned parallel to each other such that the fingers interlock without touching one another and form an array. By arranging the first electrode 20 and the second electrode 30 in such a configuration, an exemplary sensor 10 for detecting $H_2$ can be provided such that there is a greater likelihood of a conductive path being established between the first electrode 20 and the second electrode 30 subsequent to a deposition of Pd structures 50.

Regardless of the particular configuration of the electrodes on an exemplary sensor for detecting hydrogen, however, and referring again to FIG. 1A, once the first electrode 20 and second electrode 30 have been positioned at a distance from one another and affixed to the electrically-insulating support 40, a Pd structure 50 is then deposited on and contacts the first electrode 50 with at least a portion of the Pd structure 50 extending to and contacting the second electrode 30, thus creating a conductive path between the first electrode 20 and the second electrode 30. In some embodiments, the Pd structures 50 utilized in accordance with the presently-disclosed subject matter can be Pd molecules that are deposited on a first electrode 20 by electrochemically depositing the Pd on the first electrode 20. For example, in some embodiments, Pd may be deposited on the first electrode 20 by electrochemical deposition, wherein an electric current is run through a Pd solution until a sufficient amount of charge passes through the solution. In this regard, Pd deposition can be performed by attaching a wire lead to the first electrode 20 and to a potentiostat, and then holding the potential at a specified voltage versus a reference electrode.

In such embodiments, the Pd molecules forming the Pd structures 50 can further form dendritic or flower-like structures (see, e.g., FIGS. 3A and 3B) that, once deposited on a first electrode 20, may cross over to a second adjacent electrode 30 and form a conductive path between the two electrodes 20, 30. In these embodiments, the dendritic or flower-like Pd structures 50 are typically about 1-10 micrometers in length and about 0.5 to about 1.0 micrometer in width, such that, in some embodiments, the Pd structures 50 are essentially Pd nanostructures that extend from the first electrode 20 and contact a small area on the second electrode 30. Based on the conductivity of the exemplary sensors 10 for detecting $H_2$ disclosed herein, as well as the conductivity of pure Pd (94, 800 $\Omega^{-1}$ cm$^{-1}$), the estimated contact area of the Pd structures 50 on the second electrode 30 is about 83 nanometers by about 83 nanometers. As such, it is believed that the connection between the Pd structures 50 and the second electrode 30 is not through the larger micron dimensions of the Pd structures 50, but is instead through one of the smaller dendritic branches that are on the order of about 10 to about 100 nanometers or more. As shown in FIGS. 5A-5F, scanning electron microscope (SEM) images show that Pd electrodeposits upward and outward on the first electrode 20, and preferentially at the edges of the first electrode 20, such that only a small percentage of these Pd structures 50 grow long enough to make a connection to the second electrode 30 in the pre-determined time period that is used for an exemplary deposition of Pd on a first electrode 20. As such, in some embodiments, the number of connections between the electrodes 20, 30 can be between about 1 to about 25 connections per sensor 10 out of the approximately 100 to 1000 Pd structures 50 that grow into dendritic or flower-like Pd structures 50 on the first electrode 20. Furthermore, by providing a contact area on the second electrode 30 that is on the order of nanometers, it is thought that the sharper connection points provide more control over an exemplary sensor for detecting $H_2$ and also provide a more sensitive sensor that is capable of detecting lower concentrations of $H_2$ in a gas sample.

In some embodiments of the presently-disclosed subject matter, the sensors for detecting $H_2$ can thus be used in a method of detecting $H_2$ in a gas sample by: providing a sensor in accordance with the presently-disclosed subject matter; applying a voltage potential along the conductive path between the first electrode and the second electrode of the sensor; exposing the sensor to a gas sample; and detecting a decrease in conductivity along the conductive path between the first electrode and the second electrode to thereby detect $H_2$ in the gas sample. In some embodiments of the methods for detecting $H_2$ in a gas sample, which make use of a sensor of the presently-disclosed subject matter, the $H_2$ is present in the gas sample at a concentration of as low as 0.11%.

It is appreciated that hydrogen spontaneously adsorbs to Pd as atomic hydrogen and diffuses into a Pd lattice to form the more resistive $PdH_x$. In this regard, the initial α-phase Pd becomes β-phase $PdH_x$ through an α-β phase transition and the Pd lattice spacing changes throughout these phase changes, depending on the hydrogen concentration in the surrounding atmosphere. These phase transitions and changes in lattice spacing lead to measurable changes in the optical properties, resistance, and mass of the Pd, and can thus be utilized as an effective means to detect hydrogen.

For example, in one exemplary implementation of a method for detecting $H_2$ in a gas sample using a sensor of the presently-disclosed subject matter, a voltage potential (e.g., −0.3 V) can be applied to an exemplary sensor such that current flows along the conductive path between the first electrode and the second electrode that is formed by the Pd structure. When this sensor is subsequently exposed to a certain concentration of $H_2$ (e.g., a concentration above about 0.11%), the Pd structure of the sensor then transitions into the more resistive $PdH_x$ and the conductivity along the conductive path between the first and second electrode decreases reversibly such that the decrease in conductivity can then measured by methods known to those of ordinary skill in the art to thereby detect $H_2$ in the gas sample.

With further regard to the detection of $H_2$ in a gas sample, an exemplary sensor of the presently-disclosed subject matter can be utilized to determine the presence or absence of $H_2$ in a sample, but may also be used to measure the amount of $H_2$ in a particular gas sample. As such, "detecting" $H_2$, as used herein, can refer to a determination of whether $H_2$ is present or absent in a sample of interest as well as quantifying the amount of $H_2$ that is present in a sample of interest. For example, to quantify the amount of hydrogen present in a sample, a calibration curve can be obtained by measuring the response of a sensor, or the analytical signal, to known $H_2$ concentrations, i.e. standards. In these quantification methods, the analytical signal used for the detection of $H_2$ can be calculated as the percent response as described by the following equation:

%Response=$(i_r-i_b)/i_b \times 100\%$ where $i_b$ is the initial sensor baseline current in the presence of 100% $N_2$ and $i_r$ is the sensor current in the presence of a $H_2/N_2$ mixture of a certain standard percent $H_2$. A negative value is equal to a decrease in the current upon exposure to $H_2$ and vice-versa. The calibration curve is then obtained by plotting $H_2$ concentration (x-axis) versus the percent response (y-axis). From this curve, the concentration of $H_2$ in unknown samples can thus be determined.

FIG. 1B is a schematic diagram showing an exemplary method for making a switch 110 for detecting $H_2$ in accordance with the presently-disclosed subject matter. Similar to the exemplary sensor 10 shown in FIG. 1A, the exemplary switch 110 for detecting $H_2$ is fabricated by initially providing an electrically-insulating support 140 onto which a first electrode 120 and a second electrode 130 are positioned at a distance from one another and affixed. The exemplary electrically-insulating support 140 and the electrodes 120, 130 of the exemplary switch 110 can be comprised of the same materials and fabricated by the same methods that are utilized to fabricate the exemplary sensor 10 described above with reference to FIG. 1A. In the exemplary implementation shown in FIG. 1B, however, prior to depositing a Pd structure, onto the first electrode 120 of the switch 110, an organic insulating film 160 is deposited on the second electrode 130 to provide an electrically-insulating (i.e., resistive) barrier. In some embodiments, this organic insulating film 160 is comprised of an organic compound that, in the absence of hydrogen, prevents the Pd structure 150 from extending to and contacting the second electrode 130. In the presence of $H_2$, however, the Pd structure 150, which is deposited on and contacts the first electrode 120 of the exemplary switch 110 with at least a portion of the Pd structure 150 extending to and contacting the organic insulating film 160, extends through the organic insulating film 160 and contacts the second electrode 130.

In the exemplary implementation shown in FIG. 1B, the organic insulating film 160 is a polyphenol film (i.e., a polymer comprised of monomer phenol molecules that are connected to one another through carbon-oxygen-carbon bonds). Of course, other compounds capable of producing an organic insulating film can also be used without departing from the spirit and scope of the subject matter disclosed herein. For example, in some embodiments, the organic insulating film can be comprised of phenol, aniline, pyrol, or combinations thereof.

As also shown in FIG. 1B, in some embodiments, the organic insulating film 160 is deposited on the second electrode 130 of the exemplary switch 110 by an electropolymerization process in which a current is applied through a solution containing one or more monomers of an organic compound that is capable of forming an organic insulating film, such as those described above. For example, in some embodiments, the organic insulating film 160 can be deposited on the second electrode 130 of the exemplary switch 110 by electropolymerizing phenol on the second electrode 130 by cycling from 0.0 to 1.2V at 100 mV/s in a 5 mM phenol solution in 0.1 M sulfuric acid ($H_2SO_4$). Of course, to the extent is may be desired, other methods can also be utilized to deposit the organic insulating film 160 on the second electrode 130 including methods whereby the films are chemically-assembled and/or physically deposited onto the second electrode 130.

In some embodiments of the presently-disclosed subject matter, the switches for detecting $H_2$ can be used in a method of detecting $H_2$ in a gas sample. In some embodiments, a method for detecting $H_2$ in a gas sample is provided that includes providing a switch in accordance with the presently-disclosed subject matter, applying a voltage potential between the first and second electrode; exposing the switch to a gas sample, and then detecting a current between the first electrode and the second electrode to thereby detect $H_2$ in the gas sample.

As noted, in the exemplary switch of the presently-disclosed subject matter, the organic insulating film can act as a resistive barrier that reduces or prevents electrical contact between the Pd structures and the second electrode. When the exemplary switch is exposed to a gas sample containing $H_2$, $PdH_x$ forms and the Pd structures expand in volume allowing the Pd structures to expand through the polyphenol layer and make direct contact with the second electrode. The contact between the two electrodes thus causes an increase in current and forms a "switch," wherein current flows between the electrodes in the presence of a particular $H_2$ concentration, but rapidly decreases such that when the $H_2$ concentration drops below a threshold concentration negligible current flows between the two electrodes.

For example, in one exemplary implementation of a method of detecting $H_2$ that makes use of an exemplary switch, a voltage potential (e.g., −0.3 V) can be applied to an exemplary switch such that current initially flows along through the first electrode and along the Pd structure, but ceases to flow, or only flows negligibly, once the current reaches the organic insulating film. When this switch is subsequently exposed to $H_2$, such as what may be present in a gas sample of interest, the Pd structure then transitions into $PdH_x$ and expands in volume to extend through the organic insulating layer and contact the second electrode. Once contact is made with the second electrode, the current between the first electrode and the second electrode is then able to increase by 7-8 orders of magnitude such that the current between the electrodes can then be measured by methods known to those of ordinary skill in the art to thereby detect $H_2$ in the gas sample. In some embodiments, the methods of detecting $H_2$ in a gas sample utilizing a switch of the presently-disclosed subject matter can detect $H_2$ that is present in gas sample at a concentration of as low as 1.0%.

Thus, the sensors, switches, and methods of detecting $H_2$ described herein allow for electrodeposition of metals, such as Pd, to produce a sensor for controlled sensing behavior, or a combination of electrodeposition of metals and electropolymerization of one or more compounds capable of producing an organic insulating film, such as phenol, on electrodes in order to produce switches for controlled switching behavior. The sensors, switches, and methods of the presently-disclosed subject matter further allow the direct contact of a metal to the electrodes to be made by metal electrodeposition, thus eliminating the need for multistep processes involving synthesis, assembly, and contact formation which are common in electronic-based sensing devices, but also providing beneficial methods for controlling metal/organic/metal junctions in a fast parallel manner that can be used in other sensing or molecular electronics applications.

In this regard, the presently-disclosed subject matter further provides, in some embodiments, methods of fabricating a sensor for detecting an analyte of interest that can be used to fabricate useful sensors that, in some embodiments, can include metal electrode/metal structure/organic/metal electrode junctions. In some embodiments, a method for fabricating a sensor for detecting an analyte of interest is provided that includes positioning a first electrode and a second electrode at a distance from one another on an electrically insulating support; electropolymerizing a compound capable of producing an organic insulating film on the second electrode attached to the support; and electrodepositing a metal on the first electrode attached to the support such that at least a portion of the metal extends to and contacts the organic insulating film.

As one exemplary implementation of a method for fabricating a sensor for detecting an analyte on interest, a sensor for detecting an analyte of interest can be provided where, similar to the exemplary switches for detecting $H_2$ described herein above, the metal deposited on the first electrode can be Pd, and, in some embodiments, the organic insulating layer can be produced by a compound capable of producing an organic insulating film, such as phenol, aniline, pyrole, or combinations thereof. In some embodiments, the organic insulating film is a polyphenol film.

In some embodiments of the presently-disclosed methods for fabricating a sensor for detecting an analyte of interest, the thickness of the organic insulating film deposited on the second electrode is varied to change a response and recovery time of an exemplary sensor. In some embodiments, varying the thickness of the organic insulating film comprises varying the number of electropolymerization cycles, which, in some embodiments, can comprise about 4 to about 10 cycles.

For example, in one exemplary implementation of a method for fabricating a sensor for detecting an analyte of interest, where a Pd structure is deposited on the first electrode subsequent to the electropolymerization of phenol on the second electrode such that a portion of the Pd structure on the first electrode contacts the polyphenol film, it has been observed that as the number of phenol electropolymerization cycles increases, an increasingly thicker film of polyphenol is deposited on the second electrode and the response and recovery time, as well as the magnitude of response, decreases. Accordingly, for some applications where faster switching behavior is preferred, it may be desirable to use a thinner polyphenol layer, and vice versa.

Although the exemplary methods for fabricating a sensor for detecting an analyte of interest are described herein with reference to a method where the deposited metal is palladium and the organic insulating layer is comprised of organic compounds such as phenol, aniline, and/or pyrole, as a further refinement, it is contemplated that the metal deposited on the second electrode can be selected from silver or combinations of silver and palladium and that the organic insulating layer can further be comprised of various other organic molecules. For example, in some embodiments, the deposited metal can comprise a silver nanowire where the silver nanowire itself can change its conductivity in the presence of various molecules (e.g., ammonia) or can be functionalized with further materials to make the silver nanowire respond to analytes that would not typically change the conductivity of silver. As another example, in some embodiments, the organic insulating film itself can change in conductivity by reacting to a particular analyte of interest, such that, upon exposure to the analyte of interest, conductivity is increased between the metal structure contacting the organic insulating film and a change in current can be detected to thereby detect an analyte of interest. In this regard, it is contemplated that polyethylene dioxythiophene: polystyrene sulphonate (PEDOT:PSS) materials can be used to create an organic insulating layer and then used in a sensor to detect nitric oxide, methanol, ethanol, acetone, ammonia, glucose, and/or calcium ions; polyaniline (PANI) can be used to detect $NO_2$, pH, chloroform, methanol, and glucose; sulfonate-functionalized water-soluble conjugated polymers, which contain bipyridine units, can be used to detect transition metal ions; and material-based heterojunctions consisting of hexadecafluorinated nickel pthalocyanine and Nickel pthalocyanine ($Au/Ni(F_{16}Pc)/NiPc/Al$) can be used to detect $O_3$ and $NH_3$.

The above-described sensors, switches, and methods for detecting for $H_2$, as well as the methods for fabricating a sensor for detecting an analyte of interest, are important for both producing useful $H_2$ sensors and switches that exhibit controlled responses to $H_2$, but are also important for developing other sensing, nanoelectronic, and molecular electronics applications in which a metal/organic/metal junction may be desirable. Furthermore, by uniquely combining metal electrodeposition and organic compound electropolymerization at microgap electrodes, the methods and devices of the presently-disclosed subject matter provide a unique way of producing metal/organic/metal junctions. Thus, the devices and methods of the presently-disclosed subject matter provide convenient alternatives to current fabrication processes, with the added benefit that the presently-disclosed methods eliminate the need for multi-step processes involving transfer, assembly, and contact formation.

The presently-disclosed subject matter is further illustrated by the following specific but non-limiting examples.

EXAMPLES

Example 1

Fabrication and Characterization of Exemplary Hydrogen Sensors and Switches

Interdigitated gold array electrodes with 10 or 14 fingers separated by a 5 μm gap were fabricated in a clean room by photolithography on a $Si/Si_x$ substrate. Briefly, the photolithography procedure followed a positive resist procedure in which good adhesion of the photoresist was ensured by depositing hexamethyldisilazane (HDMS) onto the $Si/SiO_x$ substrate ("wafer"). A spin coater was then turned on and run at the following settings: a) 500 revolutions per minute (rpm) for 0.2 seconds (s); b) 4000 rpm for 10 s; and, (c) 0 rpm for 0.2 s. A positive resist "1813" solution was then deposited on the wafer and spun at the same settings. After coating the wafer with HDMS and 1813, the wafer was baked at 90° C. for 1 min ("soft bake"). A mask and the wafer were placed in an AB-M aligner and exposed to ultraviolet (UV) light for 6.0 s using a contact vacuum. The wafer was then soaked in toluene for 1 min and dried with a nitrogen gun. The solvent was then baked out at 90° C. for 15 s. The areas of photoresist were developed by immersing the wafer in MF-319 developer (95% water, less than 1% surfactant, and 2.2% tetramethylammonium hydroxide) for approximately 1 to 2 min.

Deposition procedures were performed using an Argon ($Ar^+$) ion source that bombards a solid target and consequently produces gas-phase atomic ions that then deposit on top of the wafer. Titanium targets were used as adhesion layers and Au was then deposited. The Au-coated wafers were immersed in acetone, and ultrasonics and a cotton swab were used for the lift-off procedure. Finally, the wafers are coated with 1813 and dicing was performed to separate the individual devices for further use.

Wire leads were attached to Au contact pads on the devices with Ag epoxy (cured 8-12 h, 80° C.), followed by further insulation with an overlayer of Torr seal epoxy (cured 8-12 h, 80° C.). The electrodes were cleaned by rinsing them in ethanol, acetone, nanopure water, and isopropyl alcohol before drying under $N_2$. The electrodes were then placed in an UVO ozone cleaner (Jelight Company Inc., Irvine, Calif.) for 10 min and were also cleaned electrochemically by cycling the electrodes in 0.1 M $H_2SO_4$ from 0.0 to 1.2 V.

FIG. 1 illustrates two methods used to electrochemically fabricate exemplary devices on interdigitated array (IDA) electrodes (10 or 14 fingers) separated by a 5 μm gap. Consistent with the exemplary methods shown in FIG. 1, the first procedure (FIG. 1A) was used to fabricate an exemplary sensor for detecting hydrogen ("$H_2$ sensor") and involved Pd electrodeposition on a first electrode (Electrode 1) from a 5 mM $PdCl_4^{2-}$ solution in 0.1 M $H_2SO_4$. Deposition was performed by hooking up one wire lead to a potentiostat and was performed in chronocoulometric mode. The potential was held at −0.1 V versus an Ag/AgCl reference electrode until $1.2 \times 10^{-3}$ coulombs of charge passed. Platinum wire was used as a counter electrode. The amount of charge passed depended on the distance between the electrodes. It was experimentally determined that $1.2 \times 10^{-3}$ coulombs was preferred for a 5 micrometer electrode separation and that a larger separation or smaller separation required a larger amount or smaller amount of charge, respectively.

The second procedure (FIG. 1B) was used to fabricate an exemplary switch for detecting hydrogen ("$H_2$ switch") and involved electropolymerization of phenol on a second electrode (Electrode 2) by cycling from 0.0 to 1.2 V at 100 mV/s in a 5 mM phenol solution in 0.1 M $H_2SO_4$ for 4 to 10 cycles. Pd was then deposited on a first electrode (Electrode 1) by following the same Pd electrodeposition procedure that was used in the first procedure.

Figure 2:
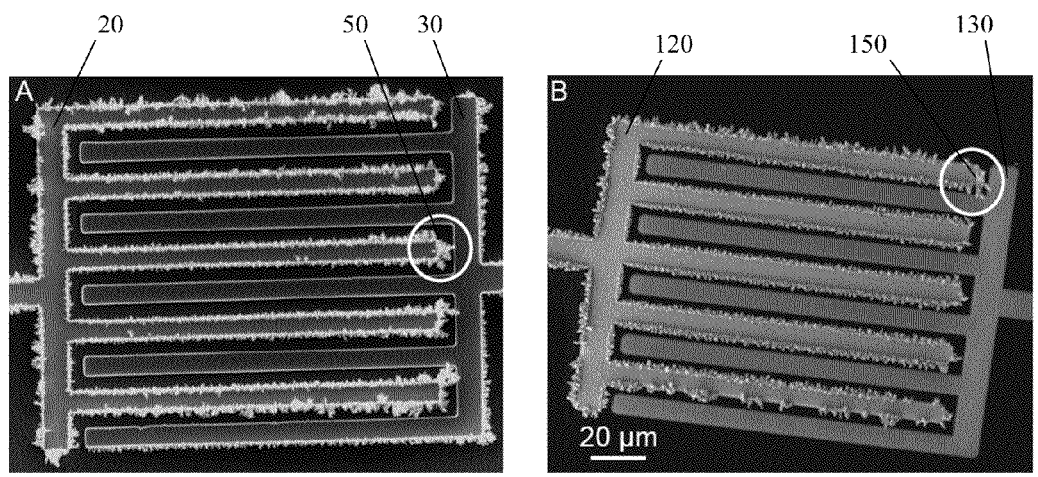
FIGS. 2A and 2B are scanning electron microscope (SEM) images of an exemplary $H_2$ sensor (FIG. 2A) and an exemplary $H_2$ switch fabricated with 10 cycles of polyphenol (FIG. 2B).
Figure 3:
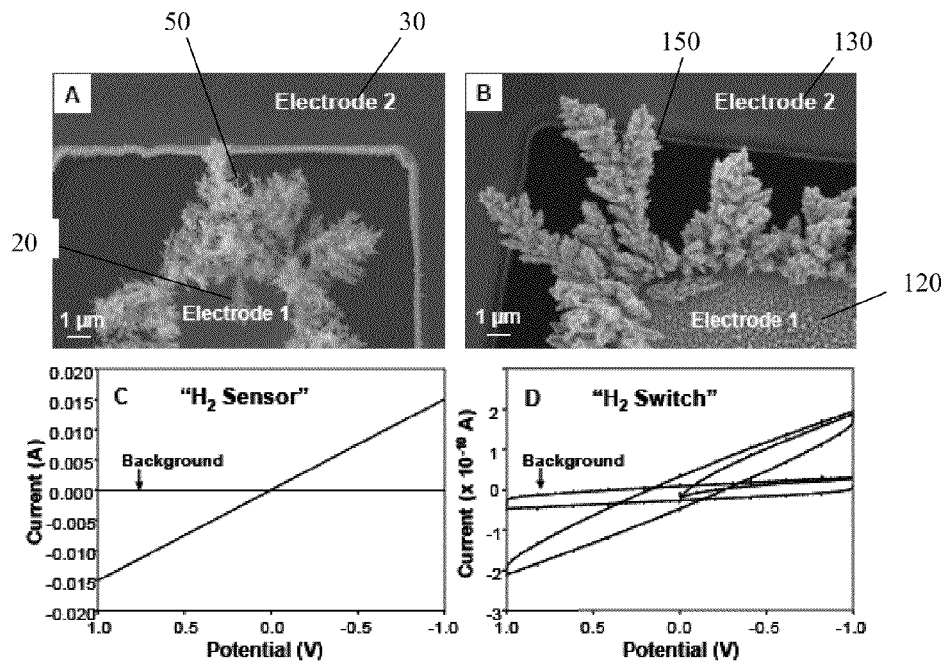
FIGS. 3A-3D are SEM images of the circled portions of the exemplary $H_2$ sensor shown in FIG. 2A and the exemplary $H_2$ switch shown in FIG. 2B (FIGS. 3A and 3B, respectively), as well as corresponding current-voltage (i-V) curves for the exemplary $H_2$ sensor (FIG. 3C) and $H_2$ switch (FIG. 3D).

FIG. 2 shows scanning electron microscopy (SEM) images of an entire 10-finger IDA for an exemplary $H_2$ sensor and for an exemplary $H_2$ switch (10 cycles of phenol). FIG. 3 shows SEM images of Pd/electrode junctions on a portion of the 10-finger IDAs depicted in FIG. 2 (circled portions), including images of portions of both an $H_2$ sensor (FIG. 3A) and an $H_2$ switch (FIG. 3B). The Pd metal deposited on Electrode 1 crossed over to Electrode 2 and has a dendritic or flowerlike structure [13]. Electrode 2 appears darker in FIG. 3B due to the presence of the insulating polyphenol film.

Figure 4:
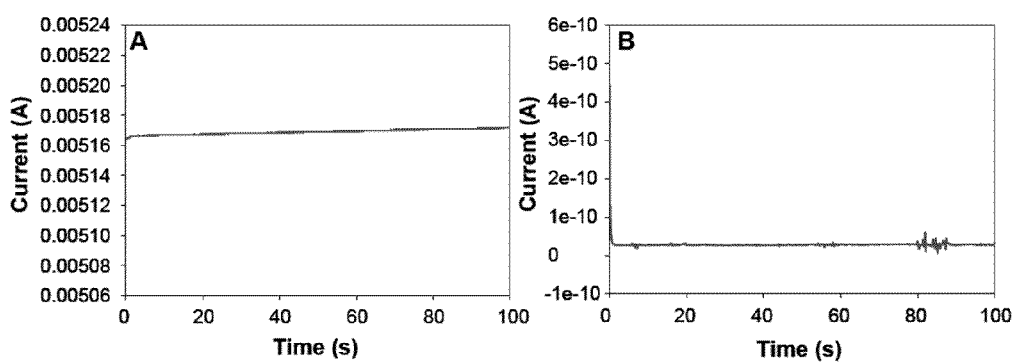
FIGS. 4A and 4B are graphs showing current-time plots for an exemplary $H_2$ sensor (FIG. 4A) and an exemplary $H_2$ switch (FIG. 4B).
Figure 5:
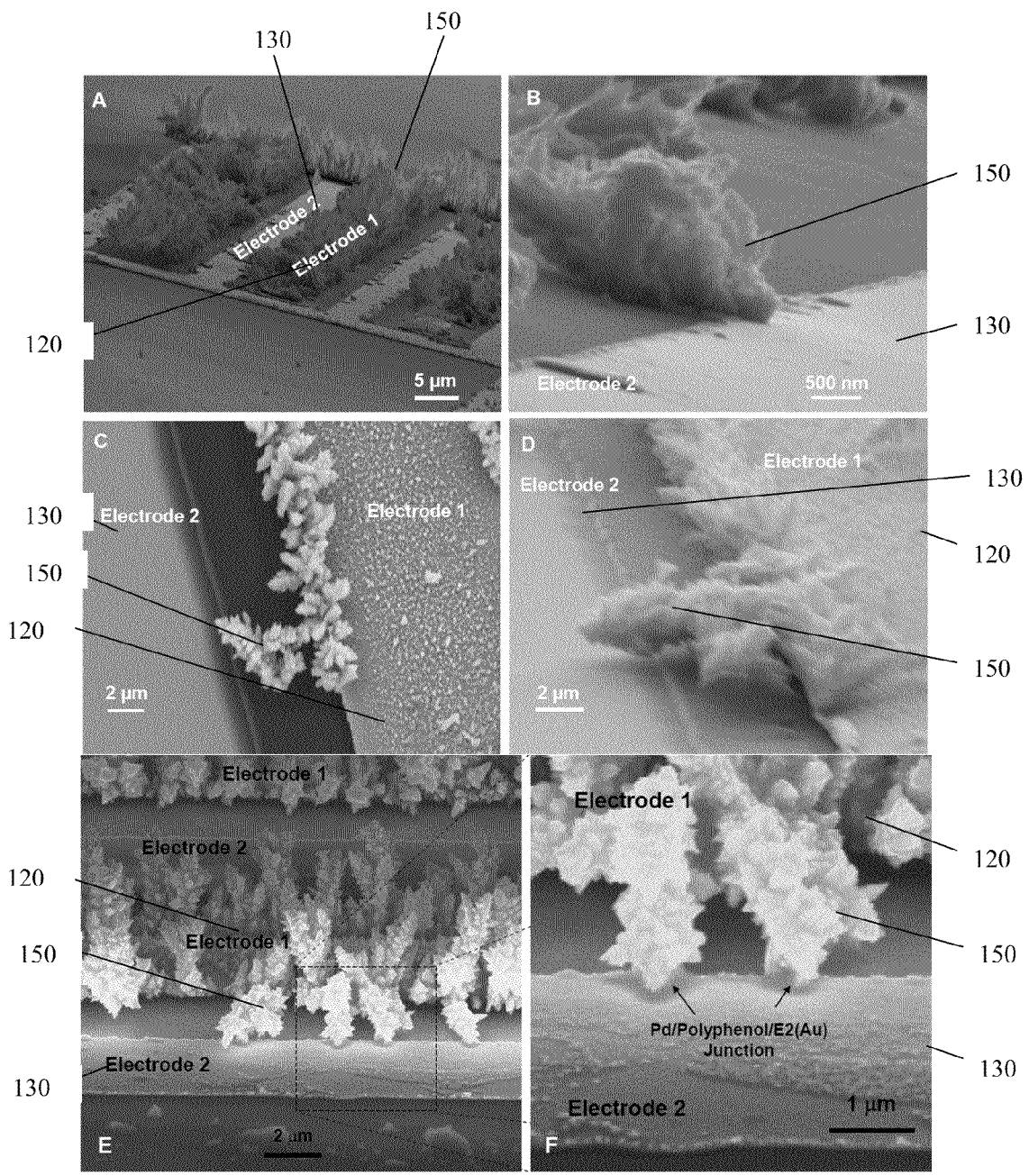
FIGS. 5A-5F are SEM images of exemplary $H_2$ switches fabricated with 10 cycles of phenol, including: a perspective view of an entire $H_2$ switch (FIG. 5A); an expanded view of a Pd structure (FIG. 5B); a top view of a single Pd structure (FIG. 5C) as compared to a side view of a Pd structure showing its proximity with a polyphenol layer on a second electrode (FIG. 5D); and, a side view of another exemplary $H_2$ switch (FIG. 5E) and an expanded image of the region depicted by the dashed box in FIG. 5E (FIG. 5F).

FIG. 3C and FIG. 3D show current-voltage (i-V) curves for an exemplary $H_2$ sensor and an exemplary $H_2$ switch, respectively. A difference between the two devices is the observed resistance. The $H_2$ sensor is ohmic, exhibiting a current of 13 mA at −1.0 V (R=77Ω), while the $H_2$ switch exhibits a current of 2.09 nA at −1.0 V (R=478 MΩ). Current time plots of the $H_2$ sensor and $H_2$ switch (FIGS. 4A and 4B, respectively) show that the current is constant in the mA range with time for the $H_2$ sensor, but exponentially decays by 1 to 2 orders of magnitude down to the 10 to 100 pA range with time for the $H_2$ sensor. Based on the known conductivity of Pd ($94,800\ \Omega^{-1}\ cm^{-1}$), the current observed for the $H_2$ sensor corresponds to a contact area of 83 nm×83 nm. This value is much smaller than the apparent contact area observed from the top view SEM images (FIGS. 2 and 3). Side-view SEM images of an exemplary $H_2$ switch (see, FIGS. 5A-5F) reveal that the Pd deposits vertically and horizontally from the first electrode and preferentially at the edges of the first electrode, indicating that some of the apparent connections viewed from the top in FIGS. 2 and 3 may not actually be in connection with the second electrode.

Table 1 provides information about the current, resistance, number of apparent connections from top views, and contact areas based on the resistance for various exemplary $H_2$ sensors and $H_2$ switches. The number of apparent connections varied while the current was within one order of magnitude for at least three samples of each type of device. The differences did not qualitatively affect the highly reproducible responses to $H_2$.

TABLE 1

Figure 6:
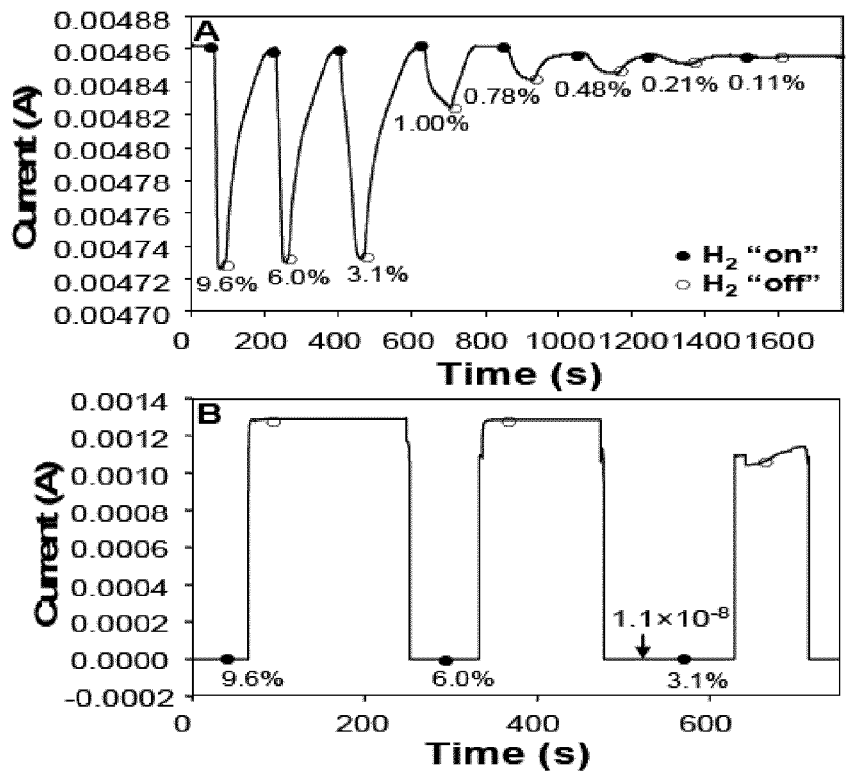
FIGS. 6A and 6B are graphs showing current-time plots of an exemplary $H_2$ sensor (FIG. 6A) and an exemplary $H_2$ switch (FIG. 6B) measured at −0.3 V in the presence of $N_2$ initially and in the presence of various concentrations of $H_2$ ($H_2$ "on", •) and 100% $N_2$ ($H_2$ "off", ○), as indicated.
Figure 8:
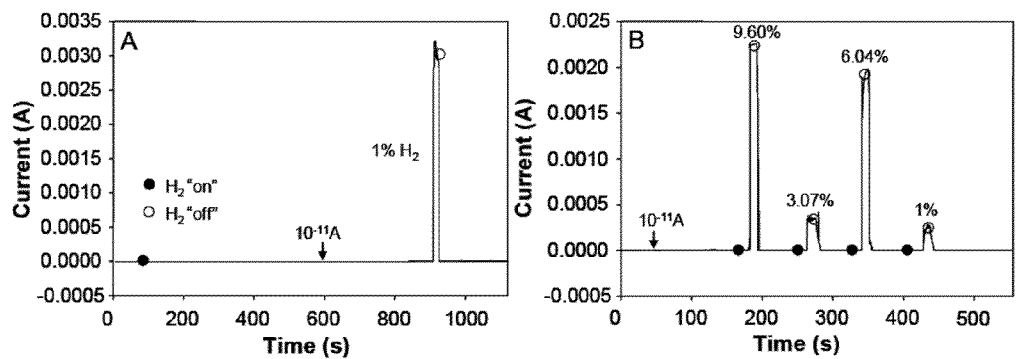
FIGS. 8A and 8B are graphs showing current-time plots for $H_2$ switches fabricated with 10 cycles of phenol (FIG. 8A) at 1% $H_2$, and a different $H_2$ switch showing shorter response and recovery times at various concentrations of $H_2$ measured at −0.3 V in the presence of $N_2$ initially and in the presence of various concentrations of $H_2$ ($H_2$ "on", •) and 100% $N_2$ ($H_2$ "off", ○), as indicated.

Number of connections, current, resistance, and contact area for exemplary $H_2$ sensors and $H_2$ switches ((*) SEM images of these samples are shown in FIGS. 2A and 2B and in FIGS. 3A and 3B); (#) current-voltage plots of these samples are shown in FIG. 3C and 3D); (†) current-time sensing plots of these samples are shown in FIGS. 6A and 6B); (‡) current-time sensing plots of these samples are shown in FIGS. 8A and 8B).

$H_2$ Sensor

| sample | # of fingers in IDA | # of apparent connections (top view) | Current at −1 V from i-V curve (A) | Resistance at −1 V (Ω) | Contact Area |
|---|---|---|---|---|---|
| 1*#† | 10 | 6 | $1.30 \times 10^{-2}$ | 76.9 | 83 × 83 nm |
| 2 | 10 | 1 | $1.37 \times 10^{-2}$ | 73.0 | 85 × 85 nm |
| 3 | 10 | 5 | $8.29 \times 10^{-3}$ | 122 | 66 × 66 nm |

H2 Switch-10 cycles Phenol

| sample | # of fingers in IDA | # of apparent connections (top view) | Current at −1 V from i-V curve (A) | Baseline current from current-time plots (pA) |
|---|---|---|---|---|
| 1 | 14 | 19 | $8.25 \times 10^{-8}$ | 10-100 |
| 2† | 10 | 3 | $1.30 \times 10^{-8}$ | 10-100 |
| 3 | 14 | 24 | $8.60 \times 10^{-9}$ | 10-100 |
| 4‡ | — | — | $1.30 \times 10^{-8}$ | 10-100 |
| 5*#‡ | 10 | 4 | $2.09 \times 10^{-9}$ | 10-100 |

Example 2

Detection of Hydrogen Using Exemplary Hydrogen Switches and Sensors

Figure 7:
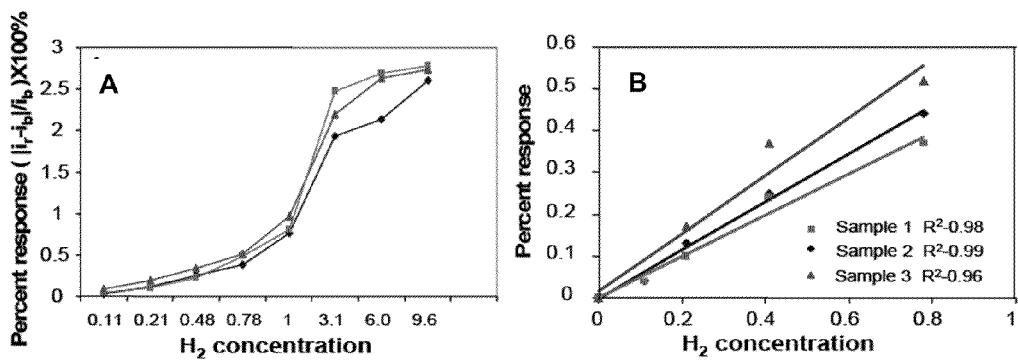
FIGS. 7A and 7B are graphs showing the percent response versus $H_2$ concentration for various $H_2$ sensors over the entire range of 0.11 to 9.6% $H_2$ (FIG. 7A) and over the linear range of 0.11 to 0.78% $H_2$. The percent response was defined as $(i_r - i_b)/i_b \times 100$, where $i_r$ is the current in the presence of $H_2$ and $i_b$ is the baseline current in the presence of $N_2$ before exposure to $H_2$.

FIGS. 6A and 6B show the current at −0.3 V as a function of time for a 10-finger IDA $H_2$ sensor and $H_2$ switch (10 cycles polyphenol), respectively, in the presence of 100% $N_2$ ($H_2$ "off", ○) and various $H_2$ concentrations as indicated in $N_2$ carrier gas ($H_2$ "on", •). The current was initially stable in 100% $N_2$ and then decreased reversibly in the presence of $H_2$ for the $H_2$ sensor, as shown in FIG. 6A. The decrease can be due to the formation of $PdH_x$, which is more resistive compared to Pd. There was a non-linear increase in the response between 1.0% and 3.1% $H_2$ that can be due to the well-known α- to β-phase-transition that occurs during the formation of PdH$_x$. Above 3.1%, the response was similar indicating hydrogen saturation of the Pd. Calibration curves from 0.0 to 0.78% H$_2$ (FIGS. 7A and 7B) for three H$_2$ sensors reveal an average slope and theoretical limit of detection of 0.58±0.11 and 0.04±0.03% H$_2$, respectively, as is also shown in Table 2. The average response and recovery time ranged from 20 to 60 s (Table 3), and the 3% change in the Pd resistance for the H$_2$ sensor at 9.6% H$_2$ was smaller than what has been previously reported in other sensing devices [3]. Without wishing to be bound by any particular theory, it is thought that the resistance increase observed with the formation of PdH$_x$ in the H$_2$ sensors is counteracted by a resistance decrease that is caused by an increase in contact area upon expansion of PdH$_x$, thus leading to a smaller increase in resistance than what would typically be expected (see, e.g., FIG. 10A).

TABLE 2

Percent responses for three different H$_2$ sensors as a function of H$_2$ concentration along with the linear slope and limit of detection for each device.

| Sample % H$_2$ | 1 % response | 2 % response | 3 % response | AVG | STD |
|---|---|---|---|---|---|
| 9.6 | 2.61 ± 0.01 | 2.74 ± 0.02 | 2.77 ± 0.06 | 2.71 | 0.09 |
| 6.0 | 2.12 ± 0.12 | 2.69 ± 0.01 | 2.64 ± 0.04 | 2.48 | 0.32 |
| 3.1 | 1.93 ± 0.23 | 2.48 ± 0.01 | 2.22 ± 0.01 | 2.21 | 0.27 |
| 1.0 | 0.76 ± 0.02 | 0.80 ± 0.02 | 0.96 ± 0.01 | 0.84 | 0.11 |
| 0.78 | 0.37 ± 0.02 | 0.44 ± 0.14 | 0.52 ± 0.02 | 0.44 | 0.08 |
| 0.48 | 0.24 ± 0.01 | 0.25 ± 0.01 | 0.37 ± 0.01 | 0.28 | 0.07 |
| 0.21 | 0.10 ± 0.01 | 0.13 ± 0.01 | 0.17 ± 0.02 | 0.13 | 0.04 |
| 0.11 | 0.04 ± 0.02 | 0.04 ± 0.01 | 0.06 ± 0.01 | 0.05 | 0.01 |
| Linear slope (% res./% H$_2$) | 0.48 | 0.56 | 0.69 | 0.58 | 0.11 |
| Limit of detection (% H$_2$) | 0.06 | 0.05 | 0.01 | 0.04 | 0.03 |

TABLE 3

Response and recovery times for three different H$_2$ sensors as a function of H$_2$ concentration.

| H$_2$ Sensor % H$_2$ | sample 1 | sample 2 | sample 3 | AVG | STD |
|---|---|---|---|---|---|
| Response time | | | | | |
| 9.6 | 17 | 29 | 24 | 23 | 8 |
| 6.0 | 29 | 25 | 24 | 26 | 3 |
| 3.1 | 31 | 37 | 25 | 31 | 4 |
| 1.0 | 57 | 61 | 58 | 59 | 2 |
| 0.78 | 46 | 61 | 58 | 55 | 8 |
| 0.48 | 55 | 50 | 59 | 55 | 5 |
| 0.21 | 47 | 53 | 51 | 50 | 3 |
| 0.11 | 30 | 38 | 34 | 34 | 4 |
| Recovery time | | | | | |
| 9.6 | 48 | 43 | 46 | 46 | 3 |
| 6.0 | 48 | 47 | 47 | 47 | 1 |
| 3.1 | 36 | 31 | 28 | 32 | 4 |
| 1.0 | 51 | 50 | 52 | 51 | 1 |
| 0.78 | 59 | 55 | 56 | 57 | 2 |
| 0.48 | 43 | 45 | 51 | 46 | 4 |
| 0.21 | 44 | 46 | 50 | 47 | 3 |
| 0.11 | 32 | 38 | 40 | 37 | 4 |

Figure 9:
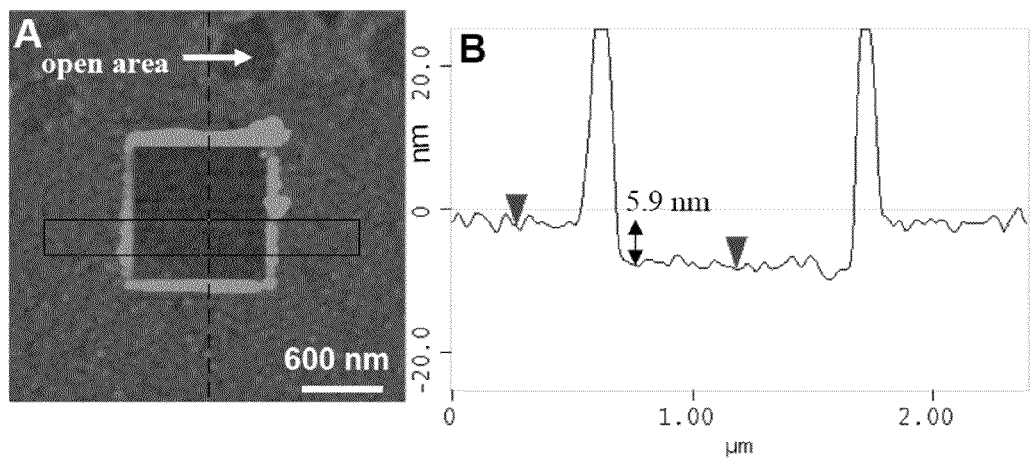
FIGS. 9A and 9B are an atomic force microscopy (AFM) image showing a portion of an electrode with electrodeposited polyphenol after scratching away an area of the polyphenol film (FIG. 9A) and a graph showing the cross-sectional analysis of the scratched area of the polyphenol film showing that the thickness is approximately 5.9 nm in that area.

The current-time plot for the H$_2$ switch in FIG. 6B is different compared to that of the H$_2$ sensor. Instead of exhibiting a decrease in current, the current dramatically increased by 7-8 orders of magnitude above 1.0% H$_2$ (see FIGS. 8A and 8B for responses of exemplary H$_2$ switches to 1.0% H$_2$). For example, at 3.1% the current increased from $1.0 \times 10^{-11}$ A to $1.1 \times 10^{-3}$ A. The dramatic increase in current can be due to a connection being made between the electrodeposited Pd and the second electrode (see, e.g., FIG. 3B) as PdH$_x$ forms and expands in volume and through the approximately 4 to 10 nm thick polyphenol layer, such as the 5.9 nm thick polyphenol layer shown in FIGS. 9A and 9B, leading to direct contact with the second electrode (see, e.g., FIG. 10B).

Figure 10:
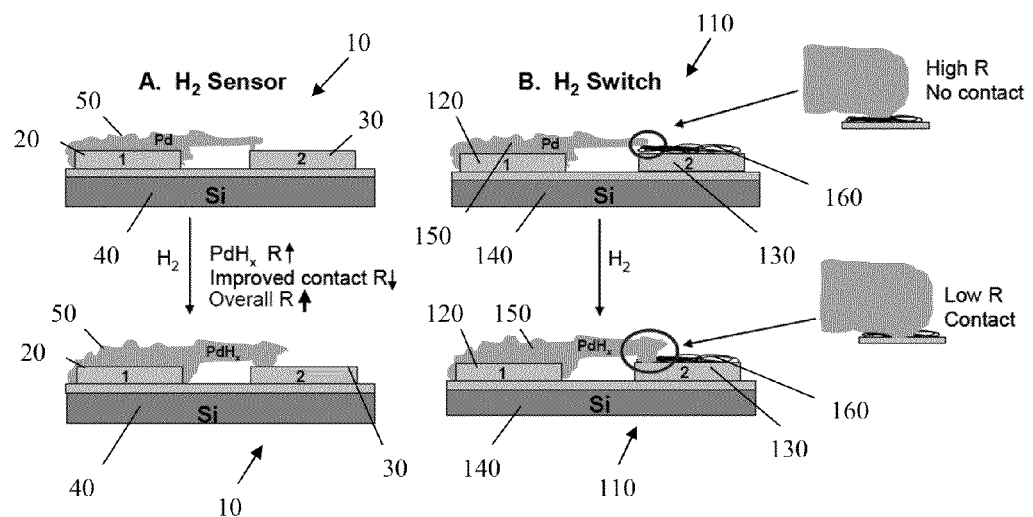
FIGS. 10A and 10B are schematic diagrams showing the mechanisms involved in an exemplary $H_2$ sensor (FIG. 10A) and an exemplary $H_2$ switch (FIG. 10B).

The mechanism depicted in FIG. 10B is supported by three observances. First, a threshold detection is observed at about 1.0% Hz, which is where the Pd transition from α-phase to β-phase occurs. Below this threshold, the volume expansion of PdH$_x$ is not sufficient to form a direct connection to second electrode. Second, the current of an exemplary H$_2$ switch above 1.0% H$_2$ is on the same order of magnitude as the current ($10^{-3}$ to $10^{-4}$ A) of the directed connected Pd in an exemplary H$_2$ sensor (see, FIG. 6A, and Tables 4 and 5), which indicates that direct contact is made in the H$_2$ switches. Third, current-voltage curves of the H$_2$ switch in the presence of H$_2$ exhibit symmetric, linear curves as does the directly connected Pd depicted in FIG. 3C, making it unlikely that Schottky barriers lead to the switching behavior.

TABLE 4

Final currents at different H$_2$ concentrations for each trial of various H$_2$ switches.

| % H$_2$ | Trial 1 Final current | Trial 2 Final current | Trial 3 Final current | AVG | STD |
|---|---|---|---|---|---|
| 10 cycles of Phenol | | | | | |
| sample 1 | | | | | |
| 9.6 | $1.29 \times 10^{-3}$ | $1.28 \times 10^{-3}$ | $1.25 \times 10^{-3}$ | $1.27 \times 10^{-3}$ | $0.02 \times 10^{-3}$ |
| 6.0 | $1.28 \times 10^{-3}$ | $1.28 \times 10^{-3}$ | $1.20 \times 10^{-3}$ | $1.25 \times 10^{-3}$ | $0.04 \times 10^{-3}$ |
| 3.1 | $1.11 \times 10^{-3}$ | $1.15 \times 10^{-3}$ | $1.10 \times 10^{-3}$ | $1.12 \times 10^{-3}$ | $0.03 \times 10^{-3}$ |
| sample 2 | | | | | |
| 9.6 | $2.47 \times 10^{-3}$ | $2.48 \times 10^{-3}$ | / | $2.48 \times 10^{-3}$ | $0.01 \times 10^{-3}$ |
| 6.0 | $1.89 \times 10^{-3}$ | $2.19 \times 10^{-3}$ | / | $2.04 \times 10^{-3}$ | $0.21 \times 10^{-3}$ |
| 3.1 | $1.73 \times 10^{-3}$ | $2.20 \times 10^{-3}$ | / | $1.97 \times 10^{-3}$ | $0.33 \times 10^{-3}$ |

TABLE 4-continued

Final currents at different $H_2$ concentrations for each trial of various $H_2$ switches.

| sample 3 | | | | | |
|---|---|---|---|---|---|
| 9 | $4.19 \times 10^{-3}$ | $3.66 \times 10^{-3}$ | / | $3.93 \times 10^{-3}$ | $0.37 \times 10^{-3}$ |
| 6 | $3.86 \times 10^{-3}$ | $2.11 \times 10^{-3}$ | / | $2.99 \times 10^{-3}$ | $1.24 \times 10^{-3}$ |
| 3 | $3.56 \times 10^{-3}$ | $1.96 \times 10^{-3}$ | / | $2.76 \times 10^{-3}$ | $1.13 \times 10^{-3}$ |
| sample 4 | | | | | |
| 9.6 | $1.19 \times 10^{-3}$ | / | / | / | / |
| 6.0 | $1.18 \times 10^{-3}$ | / | / | / | / |
| 3.1 | $1.11 \times 10^{-3}$ | / | / | / | / |
| 1.0 | $0.96 \times 10^{-3}$ | / | / | / | / |
| sample 5 | | | | | |
| 9.6 | $2.25 \times 10^{-3}$ | / | / | / | / |
| 6.0 | $1.98 \times 10^{-3}$ | / | / | / | / |
| 3.1 | $0.35 \times 10^{-3}$ | / | / | / | / |
| 1.0 | $0.28 \times 10^{-3}$ | / | / | / | / |
| 5 cycles Phenol | | | | | |
| sample 1 | | | | | |
| 9.6 | $0.42 \times 10^{-3}$ | $0.38 \times 10^{-3}$ | / | $0.40 \times 10^{-3}$ | $0.02 \times 10^{-3}$ |
| 6.4 | $0.26 \times 10^{-3}$ | $0.30 \times 10^{-3}$ | / | $0.28 \times 10^{-3}$ | $0.03 \times 10^{-3}$ |
| 3.1 | $0.17 \times 10^{-3}$ | $0.22 \times 10^{-3}$ | / | $0.19 \times 10^{-3}$ | $0.04 \times 10^{-3}$ |
| sample 2 | | | | | |
| 9.6 | $3.12 \times 10^{-3}$ | $2.97 \times 10^{-3}$ | / | $3.05 \times 10^{-3}$ | $0.11 \times 10^{-3}$ |
| 6.0 | $3.06 \times 10^{-3}$ | $2.88 \times 10^{-3}$ | / | $2.97 \times 10^{-3}$ | $0.13 \times 10^{-3}$ |
| 3.1 | $2.87 \times 10^{-3}$ | $2.56 \times 10^{-3}$ | / | $2.72 \times 10^{-3}$ | $0.22 \times 10^{-3}$ |
| 4 cycles Phenol | | | | | |
| sample 1 | | | | | |
| 9.6 | $0.74 \times 10^{-3}$ | $0.72 \times 10^{-3}$ | / | $0.73 \times 10^{-3}$ | $0.01 \times 10^{-3}$ |
| 6.0 | $0.45 \times 10^{-3}$ | $0.45 \times 10^{-3}$ | / | $0.45 \times 10^{-3}$ | $0.004 \times 10^{-3}$ |
| 3.1 | $0.30 \times 10^{-3}$ | $0.29 \times 10^{-3}$ | / | $0.29 \times 10^{-3}$ | $0.006 \times 10^{-3}$ |
| sample 2 | | | | | |
| 9.6 | $1.56 \times 10^{-3}$ | $1.49 \times 10^{-3}$ | / | $1.53 \times 10^{-3}$ | $0.05 \times 10^{-3}$ |
| 6.0 | $1.54 \times 10^{-3}$ | $1.36 \times 10^{-3}$ | / | $1.45 \times 10^{-3}$ | $0.13 \times 10^{-3}$ |
| 3.1 | $0.60 \times 10^{-3}$ | $0.62 \times 10^{-3}$ | / | $0.61 \times 10^{-3}$ | $0.02 \times 10^{-3}$ |

TABLE 5

Average final currents at various $H_2$ concentrations for $H_2$ switches as a function of the number of electrochemical cycles in phenol (for 10 cycles phenol, the average is from three exemplary $H_2$ switches (sample 1, 2, and 3); (*) the value at 1.0% $H_2$ represents the average for two devices (samples 4 and 5); for 4 and 5 cycles phenol, the average is from two different devices (samples 1 and 2); (#) the value at 1.0% $H_2$ is for one device (sample 2).

| Sample | 10 Cycles Phenol | | 5 Cycles Phenol | | 4 Cycles Phenol | |
|---|---|---|---|---|---|---|
| % $H_2$ | AVG | STD | AVG | STD | AVG | STD |
| 9.6 | $2.56 \times 10^{-3}$ | $1.32 \times 10^{-3}$ | $1.72 \times 10^{-3}$ | $1.32 \times 10^{-3}$ | $1.13 \times 10^{-3}$ | $0.39 \times 10^{-3}$ |
| 6.0 | $2.09 \times 10^{-3}$ | $0.88 \times 10^{-3}$ | $1.62 \times 10^{-3}$ | $1.34 \times 10^{-3}$ | $0.95 \times 10^{-3}$ | $0.50 \times 10^{-3}$ |
| 3.1 | $1.95 \times 10^{-3}$ | $0.82 \times 10^{-3}$ | $1.45 \times 10^{-3}$ | $1.26 \times 10^{-3}$ | $0.45 \times 10^{-3}$ | $0.16 \times 10^{-3}$ |
| 1.0 | $0.62 \times 10^{-3}$* | $0.48 \times 10^{-3}$* | / | / | $0.22 \times 10^{-3}$# | / |

Figure 11:
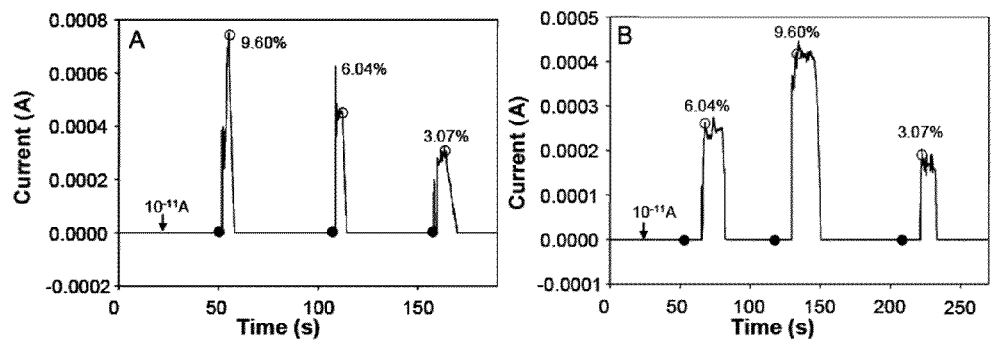
FIGS. 11A and 11B are graphs showing current-time plots for $H_2$ switches with a polyphenol film electrodeposited on a second electrode with 4 cycles of phenol (FIG. 11A) and with 5 cycles of phenol (FIG. 11B), measured at −0.3 V in the presence of $N_2$ initially and in the presence of various concentrations of $H_2$ ($H_2$ "on", •) and 100% $N_2$ ($H_2$ "off", ○), as indicated.

H₂ switches fabricated with polyphenol using 4 or 5 electrochemical cycles also operated as effective H₂ switches (FIG. 11), but with less than 100% success, which is observed in H₂ switches fabricated with 10 cycles of phenol. However, in those devices fabricated with 4 or 5 cycles of phenol, the response and recovery times were generally shorter than H₂ switches fabricated using 10 electrochemical cycles to deposit the polyphenol layer (see, Tables 6 and 7), which was attributed to faster penetration of PdHx through a thinner, more porous polyphenol film. Indeed, as the polyphenol thickness decreases, the % response increases and the response and recovery times decrease. As such, for certain applications, a thinner polyphenol layer may thus be preferable for faster and larger switching behavior.

TABLE 6

Response and recovery time at different $H_2$ concentrations for each trial of various $H_2$ switches.

| | Response time | | | | | Recovery time | | | | |
|---|---|---|---|---|---|---|---|---|---|---|
| % $H_2$ | Trial 1 | Trial 2 | Trial 3 | AVG | STD | Trial 1 | Trial 2 | Trail 3 | AVG | STD |

10 Cycles Phenol

| % $H_2$ | Trial 1 | Trial 2 | Trial 3 | AVG | STD | Trial 1 | Trial 2 | Trail 3 | AVG | STD |
|---|---|---|---|---|---|---|---|---|---|---|
| Sample 1 | | | | | | | | | | |
| 9.6 | 29 | 44 | 36 | 36 | 8 | 172 | 182 | 157 | 170 | 13 |
| 6.0 | 34 | 48 | 39 | 41 | 7 | 131 | 153 | 72 | 119 | 42 |
| 3.1 | 46 | 28 | 41 | 38 | 25 | 67 | 36 | 52 | 52 | 16 |
| Sample 2 | | | | | | | | | | |
| 9.6 | 22 | 24 | / | 23 | 1 | 68 | 76 | / | 72 | 6 |
| 6.0 | 40 | 55 | / | 48 | 11 | 67 | 73 | / | 70 | 4 |
| 3.1 | 56 | 35 | / | 46 | 15 | 72 | 41 | / | 57 | 22 |
| Sample 3 | | | | | | | | | | |
| 9.6 | 29 | 12 | / | 21 | 12 | 144 | 222 | / | 183 | 55 |
| 6.0 | 21 | 20 | / | 21 | 1 | 48 | 117 | / | 83 | 49 |
| 3.1 | 72 | 41 | / | 57 | 22 | 108 | 51 | / | 80 | 40 |
| Sample 4 | | | | | | | | | | |
| 9.6 | 27 | / | / | / | / | 76 | / | / | / | / |
| 6.0 | 32 | / | / | / | / | 63 | / | / | / | / |
| 3.1 | 48 | / | / | / | / | 48 | / | / | / | / |
| 1.0 | 830 | / | / | / | / | 27 | / | / | / | / |
| Sample 5 | | | | | | | | | | |
| 9.6 | 13 | / | / | / | / | 12 | / | / | / | / |
| 6.0 | 16 | / | / | / | / | 10 | / | / | / | / |
| 3.1 | 19 | / | / | / | / | 9 | / | / | / | / |
| 1.0 | 24 | / | / | / | / | 8 | / | / | / | / |

| | Response time | | | | Recovery time | | | |
|---|---|---|---|---|---|---|---|---|
| % $H_2$ | Trial 1 | Trial 2 | AVG | STD | Trial 1 | Trial 2 | AVG | STD |

5 Cycles Phenol

| % $H_2$ | Trial 1 | Trial 2 | AVG | STD | Trial 1 | Trial 2 | AVG | STD |
|---|---|---|---|---|---|---|---|---|
| Sample 1 | | | | | | | | |
| 9.6 | 20 | 16 | 18 | 3 | 32 | 29 | 31 | 2 |
| 6.0 | 26 | 25 | 26 | 1 | 15 | 15 | 15 | 0 |
| 3.1 | 24 | 27 | 26 | 2 | 32 | 25 | 29 | 5 |
| Sample 2 | | | | | | | | |
| 9.6 | 8 | 15 | 13 | 5 | 26 | 25 | 26 | 4 |
| 6.0 | 9 | 14 | 13 | 2 | 17 | 34 | 26 | 11 |
| 3.1 | 33 | 32 | 33 | 1 | 26 | 17 | 22 | 4 |

4 Cycles Phenol

| % $H_2$ | Trial 1 | Trial 2 | AVG | STD | Trial 1 | Trial 2 | AVG | STD |
|---|---|---|---|---|---|---|---|---|
| Sample 1 | | | | | | | | |
| 9.6 | 11 | 12 | 12 | 1 | 31 | 22 | 27 | 6 |
| 6.0 | 13 | 11 | 12 | 10 | 27 | 25 | 26 | 1 |
| 3.1 | 20 | 15 | 18 | 4 | 5 | 7 | 6 | 1 |
| Sample 2 | | | | | | | | |
| 9.6 | 7 | 9 | 8 | 1 | 22 | 23 | 23 | 1 |
| 6.0 | 14 | 6 | 10 | 6 | 22 | 23 | 23 | 1 |
| 3.1 | 23 | 22 | 23 | 1 | 15 | 11 | 13 | 3 |
| 1.0 | 110 | / | / | / | 9 | / | / | / |

TABLE 7

Average response and recovery times for $H_2$ switches to various concentrations of $H_2$ as a function of the number of electrochemical cycles in phenol. (for 10 cycles phenol, the average is from three exemplary $H_2$ switches (sample 1, 2, and 3); (*) the value at 1.0% $H_2$ represents the average for two devices (samples 4 and 5); for 4 and 5 cycles phenol, the average is from two different devices (samples 1 and 2); (#) the value at 1.0% $H_2$ is for one device (sample 2).

| $H_2$ Switch Sample | 10 Cycles Phenol | | 5 Cycles Phenol | | 4 Cycles Phenol | |
|---|---|---|---|---|---|---|
| % $H_2$ | AVG | STD | AVG | STD | AVG | STD |
| Response time | | | | | | |
| 9.6 | 27 | 9 | 16 | 5 | 10 | 2 |
| 6.0 | 37 | 14 | 20 | 10 | 11 | 1 |
| 3.1 | 47 | 9 | 30 | 5 | 21 | 4 |
| 1.0 | 426* | 570* | / | / | 110# | / |
| Recovery Time | | | | | | |
| 9.6 | 142 | 61 | 29 | 4 | 25 | 3 |
| 6.0 | 91 | 25 | 21 | 7 | 25 | 2 |
| 3.1 | 63 | 15 | 26 | 5 | 10 | 5 |
| 1.0 | 17* | 13* | / | / | 9# | / |

Throughout this document, various references are mentioned. All such references are incorporated herein by reference, including the references set forth in the following list:

REFERENCES

1. Favier, F., Walter, E. C., Zach, M. P., Benter, T., Penner, R. M. *Science* 2001, 293, 2227-2231.
2. Walter, E. C., Favier, F., Penner, R. M. *Anal. Chem.* 2002, 74, 1546-1553.
3. Sakamoto, Y., Takai, K., Takashima, I., Imada, M. *J. Phys.: condens.; Matter* 1996, 8, 3399-3411.
4. Lewis, F. A. *The Palladium/Hydrogen System*; Academic Press, Inc.: London, 1967.
5. Ibanez, F. J., Zamborini, F. P. *Langmuir*, 2006, 22, 9789-9796.
6. Ibanez, F. J., Zamborini, F. P. *J. AM. CHEM. SOC.* 2008, 130, 622-633.
7. Kong, J., Chapline, M. G., Dai, H. *Adv. Mater.* 2001, 13, 1384-1386.
8. Yu, S., Welp, U., Hua, L. Z., Rydh, A., Kwok, W. K., Wang, H. H. *Chem. Mater.* 2005, 17, 3445-3450.
9. Vanblarigan, P., Keller, J. O. *Int. J. Hydrogen Energy* 1998, 23, 603-609.
10. Peschka, W. *Int. J. Hydrogen energy* 1998, 23, 27-43.
11. North, D. C. *Int. J. Hydrogen Energy* 1992, 17, 509-512.
12. Christofides, C., Mandelis, A. *J. Appl. Phys.* 1990, 68, 1-30.
13. Cheng, C., Gonela, R. K., Gu, Q., Haynie, D. T. *Nano lett.* 2005, 5, 175-178.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A method of detecting hydrogen in a gas sample, comprising:
   providing a switch, including
      an electrically-insulating support,
      a first electrode and a second electrode positioned at a distance from one another and affixed to the support,
      an organic insulating film deposited on the second electrode, and
      a palladium structure deposited on and contacting the first electrode with at least a portion of the palladium structure extending to and contacting the organic insulating film on the second electrode, such that, upon exposure to hydrogen, the portion of the palladium structure contacting the organic insulating film extends through the organic insulating film and contacts the second electrode;
   applying a voltage potential between the first electrode and the second electrode;
   exposing the switch to a gas sample; and
   detecting a current between the first electrode and the second electrode to thereby detect hydrogen in the gas sample.

2. The method of claim 1, wherein the hydrogen is present in the gas sample at a concentration of as low as about 1.0%.

3. The method of claim 1, wherein the organic insulating film is comprised of phenol, aniline, pyrole, or combinations thereof.

4. The method of claim 3, wherein the organic insulating film is a polyphenol film.

5. The method of claim 1, wherein the first electrode and the second electrode are in an interdigitated configuration.

6. The method of claim 1, wherein the distance between the first electrode and the second electrode is about 5 micrometers.

7. The method of claim 1, wherein the palladium structure is electrochemically deposited on the first electrode.

8. The method of claim 1, wherein the organic insulating film is deposited on the second electrode by electropolymerization.

9. The method of claim 1, wherein detecting a current between the first electrode and the second electrode comprises detecting an increase in current between the first electrode and the second electrode.

10. The method of claim 4, wherein the polyphenol film is about 4 nm to about 10 nm thick.

* * * * *